US012616608B2

(12) United States Patent
Mercier

(10) Patent No.: US 12,616,608 B2
(45) Date of Patent: May 5, 2026

(54) DEVICE AND METHOD FOR MONITORING COMPLIANCE WITH A THERAPEUTIC OPHTHALMIC TREATMENT

(71) Applicant: LABORATOIRES THEA, Clermont-Ferrand (FR)

(72) Inventor: Fabrice Mercier, Chamalieres (FR)

(73) Assignee: LABORATOIRES THEA, Clermont-Ferrand (FR)

( * ) Notice: Subject to any disclaimer, the term of this patent is extended or adjusted under 35 U.S.C. 154(b) by 679 days.

(21) Appl. No.: 17/908,484

(22) PCT Filed: Mar. 2, 2021

(86) PCT No.: PCT/EP2021/055167
§ 371 (c)(1),
(2) Date: Aug. 31, 2022

(87) PCT Pub. No.: WO2021/175841
PCT Pub. Date: Sep. 10, 2021

(65) Prior Publication Data
US 2024/0024157 A1    Jan. 25, 2024

(30) Foreign Application Priority Data

Mar. 3, 2020    (FR) ...................................... 2002157

(51) Int. Cl.
*A61F 9/00*        (2006.01)
*G16H 40/20*       (2018.01)
(52) U.S. Cl.
CPC ........... *A61F 9/0008* (2013.01); *G16H 40/20* (2018.01)
(58) Field of Classification Search
CPC ...... A61F 9/0008; G16H 40/20; G16H 20/13; G16H 20/10; G16H 50/30; G16H 20/00;
(Continued)

(56) References Cited

U.S. PATENT DOCUMENTS

2016/0038695 A1    2/2016  Yu et al.
2016/0129182 A1*   5/2016  Schuster ............. A61M 15/008
                                                    702/56

(Continued)

FOREIGN PATENT DOCUMENTS

DE    10 2015 004 073    7/2016
EP    1 216 720    6/2002
(Continued)

OTHER PUBLICATIONS

International Search Report dated May 28, 2021, for PCT/EP2021/055167, 8 pp., including English translation.
(Continued)

*Primary Examiner* — Guy K Townsend
*Assistant Examiner* — Alessandro R Del Priore
(74) *Attorney, Agent, or Firm* — NIXON & VANDERHYE

(57)    ABSTRACT

Disclosed is a device for monitoring compliance with a therapeutic ophthalmic treatment using an electronic module intended to detect and transmit to a computer system data related to the actuation of a mechanical pump of a vial of an ophthalmic product. The electronic module is independent of the vial, to which it may be attached and secured. The electronic module further includes an orientation sensor. This electronic module makes it possible to characterize compliance with a treatment by the user of the vial. Also disclosed is a corresponding method for monitoring compliance with a therapeutic ophthalmic treatment, with such a module installed on a vial, and an item of computer equipment that can communicate with the electronic module.

8 Claims, 8 Drawing Sheets

(58) Field of Classification Search
    CPC .. B05B 11/108; B05B 12/004; A61M 15/008;
                    A61B 5/0022; A61B 5/4833; A61B
                                                5/7275
    See application file for complete search history.

(56)                    References Cited

U.S. PATENT DOCUMENTS

| | | | | |
|---|---|---|---|---|
| 2019/0328290 A1* | 10/2019 | Dias | ....................... | G16H 20/17 |
| 2019/0366020 A1* | 12/2019 | Tritschler | .............. | G08B 21/24 |
| 2020/0345587 A1* | 11/2020 | Aon | ................... | A61B 5/14532 |
| 2022/0047822 A1* | 2/2022 | Vokey | ................ | A61M 15/008 |
| 2024/0285878 A1* | 8/2024 | Engelhard | ............. | G16H 20/13 |

FOREIGN PATENT DOCUMENTS

| | | |
|---|---|---|
| FR | 2 739 294 | 4/1997 |
| JP | 2003-310710 | 11/2003 |
| JP | 2008-295880 | 12/2008 |
| WO | 2010/139883 | 12/2010 |
| WO | 2014/066546 | 5/2014 |
| WO | 2014/170736 | 10/2014 |
| WO | 2019/106583 | 6/2019 |

OTHER PUBLICATIONS

Written Opinion of the ISA dated May 28, 2021, for PCT/EP2021/
055167, 11 pp., including English translation.

* cited by examiner

DEVICE AND METHOD FOR MONITORING COMPLIANCE WITH A THERAPEUTIC OPHTHALMIC TREATMENT

CROSS-REFERENCE TO RELATED APPLICATION(S)

This application is the U.S. national phase of International Application No. PCT/EP2021/055167 filed Mar. 2, 2021, which designated the U.S. and claims priority to FR 2002157 filed Mar. 3, 2020, the entire contents of each of which are hereby incorporated by reference.

BACKGROUND OF THE INVENTION

Field of the Invention

The present invention relates to the field of dispensing ophthalmic products, comprising pharmaceutical solutions and other liquid ophthalmic preparations, in particular eyewashes.

In particular, the invention relates to the field of devices used to deliver ophthalmic product drops from a reservoir using a mechanical pump. Thus, the present invention relates to liquid dispensing vials, and more particularly to dispensing vials equipped with a pump system to initiate the dispense of this liquid.

The principle of such sprayers has been described in document FR-2 739 294, in an application to nasal spraying.

Description of the Related Art

The document WO 2010/139883 filed by the Applicant discloses the use of such a sprayer for an ophthalmic application, with ergonomics suitable for this use.

Indeed, in this vial type, a pump mechanism which is actuated by pressing a movable portion of the device is used in a known manner.

In order to design a vial with optimal ergonomics, which facilitates handling and which allows applying on the movable portion the force necessary for the activation of the pump, it is known to equip it with a cap to help in manoeuvring the movable portion and therefore the pump. Such a cap includes a cylindrical body which at least partially covers the reservoir of the vial, and which has at its top a planar upper wall pierced at its centre to enable the passage of the diffuser endpiece of the vial. When the cap is in place on the vial, the upper wall bears against the movable portion of the pump. Thus, the extent of the area over which one presses to actuate the pump is increased and its long-term operation is facilitated.

Different variants of caps can be used with the vial to facilitate actuation of the pump, for example in the form as claimed in the document WO 2010/139883 filed by the Applicant, which describes a cap in two portions adapted to slide towards each other parallel to the axis of the pump and each having a lateral gripping fin, which further facilitates the actuation of the portions of the pusher.

In this context, the Applicant has also filed the document WO 2014/170736, which proposes a liquid dispensing vial including a cap which enables a simple and effective marking aimed at warning the user of the first use of the vial, i.e. enabling the user to notice whether the vial has already been opened or not, in order to facilitate the conservation of the vials according to the recommendations for use.

Moreover, the effectiveness of many ophthalmic treatments depends on several parameters, in particular on compliance with the treatment dosage, and, in particular for vials with a mechanical pump, on the correct orientation of the vial during instillation of the liquid ophthalmic product.

In order to control the position of an ophthalmic product vial, in order to guarantee a correct instillation position, mechanical guides which impose a correct position on the vial by application around the eye are known, for example through the documents JP2003310710 and JP2008295880. Nevertheless, these systems are barely pleasant.

The document EP2912460 discloses a vial including a position sensor which is used to activate a drop optical sensor. When the position of the vial is correct, the device automatically triggers the means for controlling the product delivery. This system is complex, it does not involve a vial with a mechanical pump, and does not enable the user to select the instillation time.

Besides the aforementioned problems, the matter of monitoring compliance with the dosage remains unresolved in the prior art. Moreover, this strict control of compliance with the dosage turns out to be not necessary for all treatments or for all patients, but could on the contrary be useful over a quite long period during which several vials of an ophthalmic product are successively used.

Thus, the present invention aims to propose a device allowing solving all or part of the aforementioned problems.

SUMMARY OF THE INVENTION

To this end, a device for monitoring compliance with an ophthalmic therapeutic treatment is proposed in the invention. This device includes an electronic module intended to detect data relating to the actuation of a mechanical pump of a vial of a liquid ophthalmic product including a main body including a reservoir, a dispensing head and a mechanical pump, the dispensing head being mounted on the main body, the dispensing head including a movable portion a movement of which relative to the main body actuates the mechanical pump to sample the liquid ophthalmic product present in the reservoir.

In the proposed device for monitoring compliance with a treatment, the electronic module is independent of the vial so that it could be attached and fastened thereto.

By "independent", it should be understood that the module could be attached and fastened to the vial. Where appropriate, the module could then be detached off the vial. Hence, it is a module distinct from the vial. The module, including its shell or its case where appropriate, is not formed integrally with a portion of the vial. When it is attached and fastened to a suitable vial, the module is in mechanical interaction with the vial, so that an actuation of the pump of the vial actuates the module as detailed hereinafter.

The electronic module includes an actuator configured to be set in motion by the movement of the movable portion. The electronic module includes a sensor configured so as to be actuated by the movement of the actuator. The electronic module further includes an orientation sensor configured to provide information relating to the orientation of the electronic device. The electronic module further includes a communication port, wired or wireless, configured for the transfer of data relating to the actuation of the mechanical pump of the vial and the data relating to its orientation towards an external computer equipment.

The compliance monitoring device also includes the external computer equipment configured to communicate with said electronic module, the computer equipment executing software enabling temporal monitoring of the actuations of the actuator of the electronic module, which correspond to a delivery of the ophthalmic product.

Thus, the proposed electronic module can form, in combination with a vial of a pre-existing type, an ophthalmic product vial enabling the collection of data relating to compliance with a treatment, and possibly a connected vial.

The proposed electronic module does not require the development of a new pump vial. It is particularly suitable for equipping a vial with a mechanical pump including a delivery assist device, of a type already commercialised by the Applicant, in order to form, in combination with suitable computer equipment, a device for monitoring compliance with an ophthalmic therapeutic treatment.

The orientation sensor configured to provide electronic module orientation information may include at least one accelerometer configured to provide information on the orientation of the electronic module.

An accelerometer allows characterising the orientation of the vial equipped with the module. Yet, the orientation of the vial when dispensing the product is important. In particular, for a vial with an axial actuation mechanical pump, the vial should generally be vertical when instilling the product into the eye. The installation remains correct within a relatively limited range of angles around the vertical, whereas an incorrect inclination of the vial could lead to an incorrect instillation (insufficient amount of product delivered or received by the eye, inaccurate drop point of the delivered drop, etc.).

In such a device for monitoring compliance with an ophthalmic therapeutic treatment, the computer equipment executing the software may be configured to provide the user with information on the correct or incorrect orientation of the electronic module, and therefore accordingly of a vial equipped with said electronic module, when the actuator is actuated.

Indeed, the orientation of the vial when dispensing the product is an important parameter in compliance with a treatment, and this information could be used to qualify compliance, and/or for teaching the user to use the vial correctly.

The information on the correct or incorrect orientation of the electronic module may include visual information and/or audible information.

Moreover, the electronic module or the computer equipment executing the software may be configured to emit in real-time a signal indicating that the module has a correct orientation for dispensing a liquid ophthalmic product by a vial equipped with said electronic module.

In particular, the electronic module may be adapted to transfer the data towards the external computer equipment according to a Bluetooth™ protocol.

The wireless transmission of the data measured and/or collected by the module allows interfacing the electronic module with an external system, which enables the processing and visualisation of the data. It may consist in monitoring compliance with the treatment, by the patient or his doctor, or in teaching the user to carry out correct, and therefore effective, instillations of the ophthalmic product.

The electronic module may include an electronic memory adapted to store data relating to the actuations of the actuator, in particular the number, the date and the time of the actuations.

Thus, the measured data include the basic data for controlling compliance with the treatment.

In such a device, the computer equipment executing the software could enable recording of a dosage, and the provision to the user of a comparison between the recorded dosage and the data relating to the actuation of the actuator of the electronic module transmitted to the computer equipment.

Thus, a complete solution is proposed in the invention allowing comparing the treatment actually followed by the patient with the dosage that has been prescribed to him.

In some embodiments, the computer equipment executing the software can calculate, on the basis of the data transmitted by the module, a compliance score and indicate it to the user.

Thus, the invention enables the user to check that his instillation gestures are correct. If this is not the case, the user can also correct it, in order to improve the effectiveness of his treatment. The instillation time data may be combined with data characterising the instillation gestures to calculate a "score" or a "mark", that the user will naturally pursue to improve during his treatment. Thus, the device has an educational, and possibly playful, effect for the user.

For example, the computer equipment may be a smartphone or a tablet, and the software is then an application.

The present invention also relates to a method for monitoring compliance with an ophthalmic therapeutic treatment. This method includes the following steps:

providing an ophthalmic product vial and a device for monitoring compliance with an ophthalmic therapeutic treatment as described hereinabove, fastening the electronic module on the ophthalmic product vial;

determining, over time, correct product instillations and incorrect product instillations, according to compliance parameters, informing a user (who could be the person who uses the device or a prescriber of the therapeutic treatment), on the results of the step of determining the correct product instillations and the incorrect product instillations.

In particular, the compliance parameters may include the detection, within a given time frame, of one or more actuations of the vial and/or the detection of a proper orientation of the vial.

The method for monitoring compliance with a therapeutic treatment may further include a step of calculating a compliance score as a function of the compliance parameters, and a step of informing the user on the temporal progression of said compliance score.

In the context of the present invention, it is remarkable that an independent electronic module, and therefore adapted to be attached to an ophthalmic product vial, has many advantages. This allows equipping a vial only when necessary. For example, when the patient has difficulties following the prescribed dosage, or at the beginning of a treatment when it is necessary to ensure that the dosage or other parameters of administration of the product are correctly complied with. Moreover, the electronic module may be transferred from one vial to another, in order to follow the treatment of a user over a long period (longer than the duration of treatment offered by a vial). Finally, this is economical, in that the module could be offered for a wide range of products, without having to provide for different ranges of vials, per product and depending on whether a transmission or a storage of the actuation data of the vial is desired or not.

In particular, the module could be adapted to a vial in which the movable portion is movable in axial translation relative to the main body. The sensor may be a contactor, the actuator being guided in translation according to said axial direction and including a first bearing surface on the movable portion and a second bearing surface on the contactor.

The actuator may be in the form of a rod extending according to the axial direction, the rod including a first end forming the first bearing surface, and a second end, opposite to the first end, forming the second bearing surface.

The electronic module may include a spring tending to return the actuator back in a rest position. The contactor is then advantageously open when the actuator is in the rest position.

A contactor is a simple and economical device, allowing having reliable information on the actuation of the pump of a vial with a mechanical pump. Furthermore, a contactor is relatively simple to implement with such a vial, thanks to the axial actuation of the pump, which could be used to generate an axial press on the contactor. A contactor also has the advantage of being able to serve as a switch for the module, so that the module consumes only electrical energy, supplied by a cell or battery, when the contactor is closed.

The electronic module may include a case forming an inner volume for receiving at least one electronic board, said case including a base and a cover, said base including an opening enabling the passage of the actuator.

Thus, the electronic module is correctly protected from the external environment, with the actuator alone protruding from the case. In some embodiments, the cover of the case may be removable, but it will more generally be non-removable, for example sealed upon mounting of the module. The electronic module is maintenance-free. In particular, in preferred embodiments, it may be fitted with a cell enabling the power supply of the module for example for several weeks, several months, and possibly several years.

An assembly including a vial of a liquid ophthalmic product and an electronic module as defined before is also proposed. The vial includes a main body including a reservoir and a bottom, a dispensing head and a mechanical pump, the dispensing head being mounted on the main body, the dispensing head including a movable portion, a movement of which actuates the mechanical pump to sample the liquid ophthalmic product present in the reservoir. The electronic module is attached and fastened either to the main body or to the dispensing head, so that the movement of the movable portion relative to the main body to sample the liquid ophthalmic product present in the reservoir sets the actuator of the electronic module in motion.

The movable portion of such a vial may be movable in axial translation relative to the main body. This vial may include a delivery assist device, the main body including a first portion of the delivery assist device which cooperates with the reservoir, the first portion of the delivery assist device including a first lateral fin, the dispensing head including a second portion of the delivery assist device which cooperates with the movable portion, the second portion of the delivery assist device including a second lateral fin, the first fin and the second fin being substantially facing each other to enable the axial movement of the movable portion when a force is exerted between the two fins tending to bring them axially close to each other.

In such an assembly, during the axial movement of the movable portion, the actuator could bear on, and actuated by, the second portion of the delivery assist device.

In particular, the first lateral fin may include a hole through which the actuator of the electronic module passes, said actuator bearing during the axial movement of the movable portion on a radial excrescence of the second portion of the delivery assist device.

Other particularities and advantages of the invention will appear further in the description hereinafter.

BRIEF DESCRIPTION OF THE DRAWINGS

In the appended drawings, given as non-limiting examples.

DESCRIPTION OF THE PREFERRED EMBODIMENTS

Figures 1, 2, 3, 4:
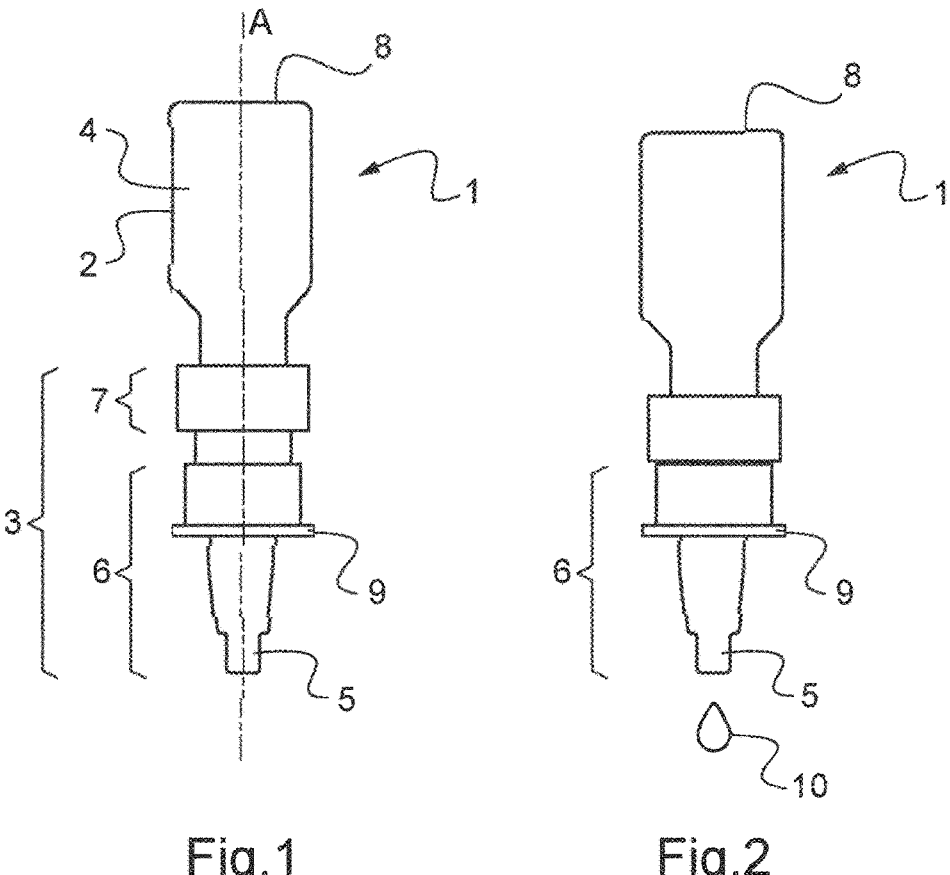
FIG. 1 represents, according to a schematic view, a liquid ophthalmic product vial including a mechanical pump, in a first configuration.
FIG. 2 represents, according to a schematic view, the vial of FIG. 1 in a second configuration.
FIG. 3 represents, according to a schematic view, a liquid ophthalmic product vial including a delivery assist device.
FIG. 4 represents, according to a schematic three-dimensional view, the vial of FIG. 3.

FIG. 1 represents a liquid ophthalmic product vial including a mechanical pump. Such a vial is known in the prior art for dispensing a nasal or ocular liquid product. The vial 1 includes a main body 2 and a dispensing head 3. The main body 2 forms a reservoir 4, intended to contain a liquid product, for example a liquid ophthalmic product. The dispensing head 3 includes an endpiece 5, provided at its end with a dispensing orifice through which the liquid product comes out during dispensing thereof. The dispensing head 3 includes a movable portion 6 and a fixed portion 7. The fixed portion 7 being rigidly linked to the main body 2 of the vial 1, the movable portion 6 is movable relative to said main body 2. More particularly, the movable portion 6 can be translated according to a so-called axial direction, determined by the main axis A of extension of the vial 1. In particular, bringing the movable portion 6 close to a bottom 8 of the main body drives a mechanical pump contained in the vial. The actuation of the mechanical pump results in sampling of the liquid present in the reservoir 4 and dispensing thereof through the dispensing endpiece 5. In order to help the user actuate the pump, i.e. to bring the movable portion 6 close to the bottom 8, the movable portion 6 includes a collar 9 forming a support plane substantially orthogonal to the axial direction of actuation.

FIG. 1 represents the vial 1 in a configuration at rest, which it tends to adopt in the absence of actuation.

FIG. 2 represents the vial 1 of FIG. 1 in an actuation configuration, i.e. when the movable portion is actuated by creating a force tending to bring it close to the bottom 8. For example, such a force is obtained by pinching between the fingers of one hand of the user, positioned on the bottom 8 and under the collar 9. When reaching the actuation configuration of FIG. 2, a product drop 10 or jet is delivered by the endpiece 5 of the vial 1.

The vial of FIGS. 1 and 2 forms a first example of a vial on which the present invention could be applied.

FIG. 3 and FIG. 4 represent a liquid ophthalmic product vial including a delivery assist device. Indeed, the vial of FIGS. 1 and 2 may turn out to be difficult to actuate, in particular when dispensing an ophthalmic product, such a dispense requiring an accurate holding of the vial in position.

A proper hold in position is obtained by improving the general ergonomics of the vial and by facilitating the application of the force necessary for actuation thereof.

The principle developed in the vial of FIGS. 3 and 4 consists in equipping the vial 1 with at least two lateral fins, substantially orthogonal to the axial direction of actuation of the pump and of the vial 1.

In particular, the vial 1 includes a first lateral fin 11 allowing holding of the fixed portion 7 of the vial 1 in position and a second lateral fin 12 allowing moving the movable portion 6 of the vial 1 according to the axial direction. More generally, bringing the first lateral fin 11 and the second lateral fin 12 close to each other according to the axial direction results in the actuation of the mechanical pump of the vial 1.

The first lateral fin 11 and the second lateral fin 12 are substantially opposite each other, in two axially distant planes. This facilitates the application of a force tending to bring them close to each other. In the example represented herein, the first lateral fin and the second lateral fin substantially have an identical length. Other fin configurations may be used, and are compatible with the present invention.

In practice, the vial of FIGS. 3 and 4 may include the vial of FIGS. 1 and 2, on which is added a cap to facilitate the actuation of the pump. In particular, the vial of FIGS. 1 and 2 is represented in dotted lines in FIG. 4, installed in a cap in two portions forming a delivery assist device.

Thus, the main body of the vial of FIGS. 3 and 4 includes a first portion of the delivery assist device 13 including the first lateral fin 11, which is attached to the reservoir of FIGS. 1 and 2. In particular, the first portion of the delivery device 13 forms the bottom 8 of the vial 1. The first portion of the delivery assist device 13 may be configured (apart from the first lateral fin 11) essentially in the form of a vat whose internal shape is adapted to receive the reservoir 4.

In turn, the dispensing head 3 of the vial of FIGS. 3 and 4 includes, besides the fixed portion 7 and the movable portion 6, a second portion of the delivery assist device 14. The second portion of the delivery assist device 14 includes the second lateral fin 12. The second portion of the delivery assist device 14 is (except the second lateral fin 12) essentially in the form of a barrel including a proximal area of the bottom 8 cooperating with the first portion of the delivery assist device 13 and a distal flange 18 of the bottom 8 which bears on the collar 9 of the movable portion 6 of the dispensing head.

The first portion of the delivery assist device 13 and the second portion of the delivery assist device 14 are, in the represented example, guided in axial translation relative to each other by means of a groove 15 of the second portion of the delivery assist device 14 in which a pin 16 of the first portion of the delivery assist device 13 is guided. A radial excrescence 17 of the second portion of the delivery assist device prevents the pin 16 from coming out of the groove 15.

The endpiece 5 of the vial 1 protrudes from the distal open end 19 of the second portion of the delivery assist device 14. In FIGS. 3 and 4, the vial 1 is represented equipped with a cap 20 which plugs and protects the endpiece 5. Other cap configurations are of course known, in particular including a first opening visual indicator.

The vial of FIGS. 3 and 4 forms a second example of a vial on which the present invention could be applied, and forms a preferred application thereof.

As visible in FIG. 4, the vial 1 has a minor optional adaptation (in comparison with the vial commercially available in the prior art) enabling the use on this vial of an electronic module forming a preferred embodiment of the invention. This adaptation consists of the formation of a hole 21 in the first lateral fin 11, in the immediate proximity of the wall of the main body 2 of the vial 1, the use of which is explained hereinafter.

Figure 5:
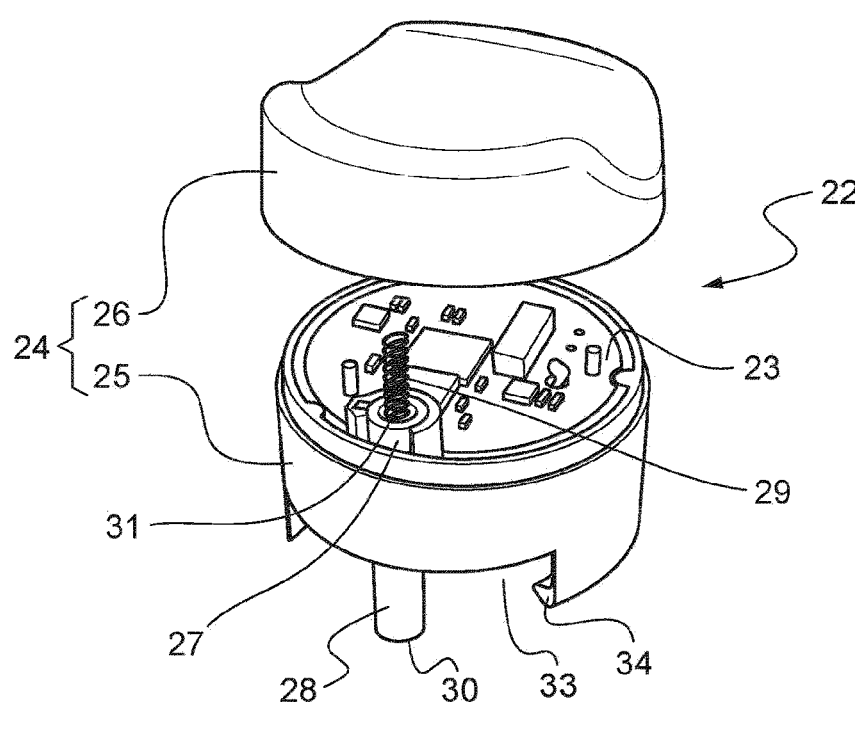
FIG. 5 represents, according to a schematic three-dimensional view, an electronic module in accordance with a proposed embodiment.

FIG. 5 represents an electronic module 22 in accordance with an embodiment of the invention. The electronic module 22 includes one or more electronic boards 23, mounted in a case 24. The case includes, in the represented example, a base 25 and a cover 26. Typically, the base 25 may include pads for receiving and holding the electronic board 23. Once the electronic board 23 is positioned in the base, the case is closed by placing the cover 26. Advantageously (yet not necessarily), the cover 26 is sealed on the base 25, making any subsequent opening impossible. Fusible pads could be used to achieve this sealing.

The base 25 includes an opening 27 through which an actuator 28 comes out of the case 24. The shape of the opening corresponding to that of the actuator 28, the actuator 28 is, in the represented example, perfectly guided in translation in the opening 27. In this case, the actuator 28 is in the form of a cylindrical rod. A spring 29, in this case a helical spring tends to bring the actuator back in a rest position, in the absence of any external force applied on the actuator 28.

The electronic module 22 includes a sensor intended to be activated by the axial movement of the actuator 28. Advantageously, the sensor is a contactor. Thus, the rod-shaped actuator 28 of the embodiment represented herein has at its first end, located outside the case 24, a first bearing surface 30. The first bearing surface 30 is intended to come into contact with and bear on a movable portion element 6 of the dispensing head. The rod-shaped actuator 28 has at its second end, located in the case 24, a second bearing surface 31, intended to come into contact with and press on the contactor. Thus, the second bearing surface 31 causes a press or a release of the contactor when a force is applied on the first end 30 of the actuator 28, when this force is enough to compress the spring 29, and when the movement imposed to the actuator 28 has a sufficient amplitude.

Thus, in the rest position of the actuator 28, the contactor is open, whereas when the actuator is pushed into the case, the contactor is closed. Depending on the considered contactor technology and the configuration of the electronic module 22, the closure of the contactor may, be caused by a press or a release on the contactor.

The positioning of the electronic components of the module in a case offers them suitable protection against impacts and other external mechanical stresses, but also against particles and splashes.

This is particularly important for a module that is potentially intended to be used successively on several vials. In particular, the indirect actuation of the sensor (for example of the contactor) using an actuator which is the only element passing through the case of the module, with a very small functional clearance, allows protecting the sensor against a deterioration of its performances. In particular, particles or dust on the sensor could distort the measurement, and/or create false contacts.

The electronic module 22 includes an electrical energy source, in the form of a cell or a battery. A battery can ensure a very long autonomy to the sensor, several weeks, several months, and possibly several years of treatment. In particular, when the electronic module 22 includes a contactor as a sensor, the electronic module 22 may be configured to consume energy only when the sensor is actuated. For example, the closure of the sensor corresponding to the detection of an actuation of the actuator, and therefore of the vial on which it is mounted, may cause the supply of the electronic module 22 with power.

Figure 6:
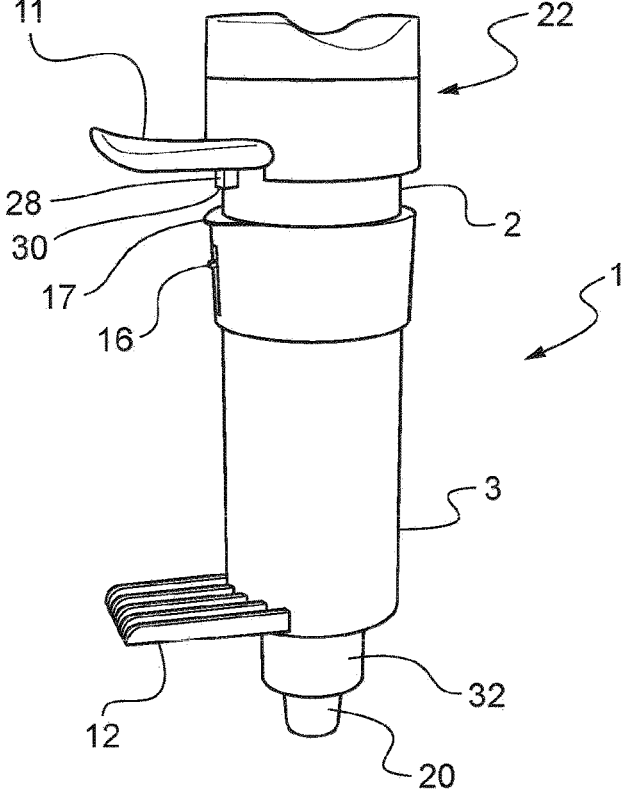
FIG. 6 represents, according to a schematic three-dimensional view, the module of FIG. 5 installed on the vial of FIG. 3.

FIG. 6 represents the module of FIG. 5 installed on the vial similar to that of FIGS. 3 and 4. The vial represented in FIG. 6 differs from that of FIGS. 3 and 4 only in that the cap 20 has a different shape and has a ring 32 allowing showing whether the vial has already been opened or not.

In the example represented herein, the electronic module 22 is fastened on the bottom 8 of the vial 1, by form-fitting and by clipping on the first lateral fin 11. Clipping of the electronic module 22 on the first portion of the delivery assist device 13 makes these two elements secured to each other, and fixed relative to each other. For this purpose, the base 25 of the case 24 is provided with a notch 33 forming two fastening legs 34 adapted to be blocked under the first lateral fin 11.

The actuator 28 passes through the hole formed in the first lateral fin 11. When the vial is actuated by bringing the first lateral fin 11 and the second lateral fin 12 close to each other according to the axial direction (parallel to the main axis A of the vial), the first bearing surface 30 of the actuator comes into contact with the radial excrescence 17 of the second portion of the delivery assist device 14. The movement of the electronic module relative to the radial excrescence 17 being carried on, the latter applies by reaction a force on the actuator 28 which pushes the actuator into the case 24. The contactor of the electronic module 22 is then actuated.

The hole in the lateral fin 11 guarantees a correct positioning of the actuator and of the module with respect to the vial. Furthermore, it participates in the proper translational guidance of the actuator.

Of course, fastening the module to the main body of the vial, at a location other than its bottom and/or by a means other than clipping may be considered without departing from the scope of the invention.

In particular, the electronic module may be configured so that the case it includes is installed on the side, and not at one end, of the equipped vial. This limits the increase in length of the vial related to the installation of the electronic module.

The actuation of the contactor (or another sensor) of the electronic module 22 causes either the recording of data relating to this actuation, or the wireless transmission of this data, or both. The recording of the data may be carried out on a memory that the electronic module 22 includes where appropriate.

The transmission of the data, in real-time or occasionally after recording, is advantageously carried out wirelessly, for example according to a Bluetooth™ protocol, advantageously Bluetooth Low Energy™. To this end, the electronic module 22 is provided with a wireless communication system, including a wireless communication port ensuring the transfer of data. In an alternative embodiment, a communication via a wired port may be used.

Figure 7:
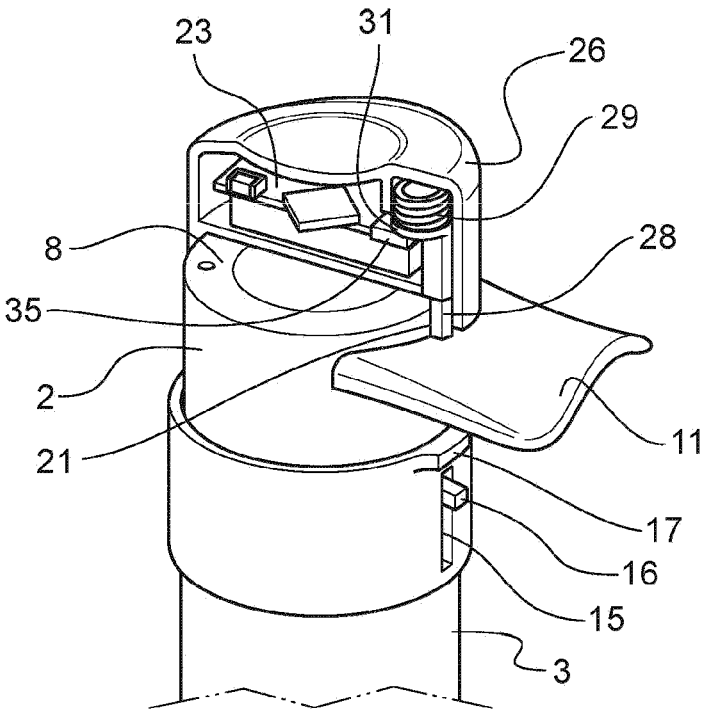
FIG. 7 represents, according to a three-dimensional detail view in partial section, the assembly of FIG. 6.

In the embodiment of FIG. 7, a contactor 35 is under the pressure of the second bearing surface 31 of the actuator 28, under the effect of the spring 29, when the actuator is in its rest position. Setting of the actuator 28 in motion upon a press thereon, via the first bearing surface 30, on the radial excrescence 17 of the second portion of the delivery assist device 14, releases the pressure exerted on the contactor 35 by the second bearing surface 31, which causes the closure of the contactor, and the detection of the actuation of the vial.

The data relating to the action may vary. The first of the data relates to information on the mere actuation of the vial. A time information may be associated with this information, typically information on the date and time of the detected actuation, or information relating to the time elapsed since the previous actuation. The actuation information may be accumulated over time, in order to determine a number of actuations during an intake (during an instillation sequence), or a total number of actuations.

The module may include one or more accelerometers. Alternatively or complementarily, other position and orientation sensors, in particular gyroscopes, may be used. The accelerometer allows determining the orientation of the electronic module in space, and in particular its orientation with respect to the vertical. For the instillation to be correct, the vial should be oriented vertically, i.e. the main axis A of the vial should be aligned with the vertical, or at the very least included within a given range of angles around the vertical. This information is determined using the accelerometer at the time of actuation of the vial, and may be associated with data relating to the actuation, in particular with time information.

Thus, in some embodiments, the electronic module could allow determining when an instillation has been carried out, how many product drops have been delivered on this occasion, and what was the orientation of the vial for each delivered drop.

Figure 8:
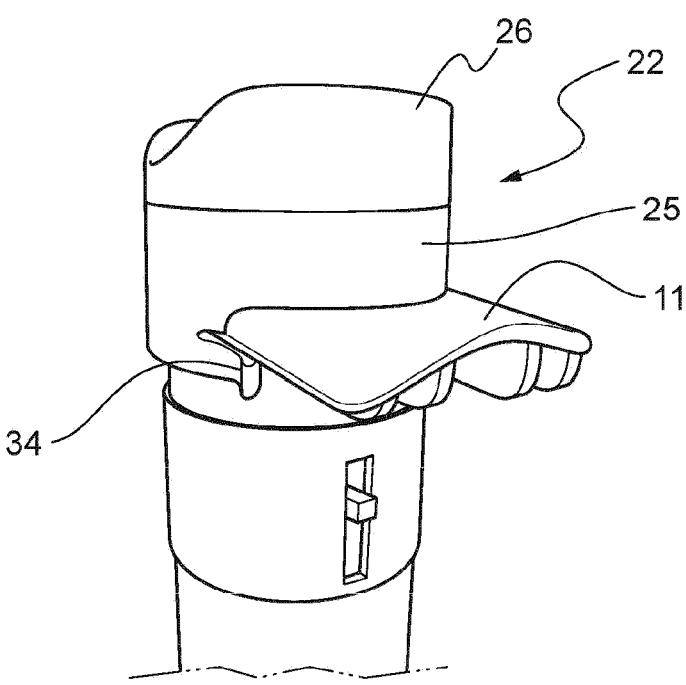
FIG. 8 represents, according to a schematic three-dimensional view, another electronic module installed on a vial similar to that of FIGS. 3 and 4.

FIG. 8 represents another electronic module installed on the vial of FIGS. 3 and 4. This embodiment differs from that of FIGS. 5 to 7 in that the base 25 of the case 24 of the electronic module 22 includes tabs 34 for clipping on the first lateral fin 11 which have larger dimensions and which extend partially laterally, under said first lateral fin 11. The optional cambered shape of the first lateral fin 11 allows for an easy clipping by axial pressure on the module 22, this pressure and said cambered shape having the effect of spacing the tabs 34 apart. The removal of the electronic module 22, for example in order to install it on another vial, is carried out by spacing the tabs 34 apart from each other, which clears the tabs from the first lateral fin 11. Thus, fastening of the electronic module 22 is made more reliable, and the clearances between the electronic module 22 and the vial are limited.

The invention has been illustrated in FIGS. 5 to 8 according to embodiments in which the electronic module 22 is fastened to the main body 2 of the vial. Similarly, fastening of the electronic module 22 to the dispensing head 3, in a configuration of the electronic module 22 according to which the relative movement between the main body 2 and the movable portion 6 enables the actuation of said electronic module 22. Such an embodiment is illustrated in FIG. 9.

Figure 9:
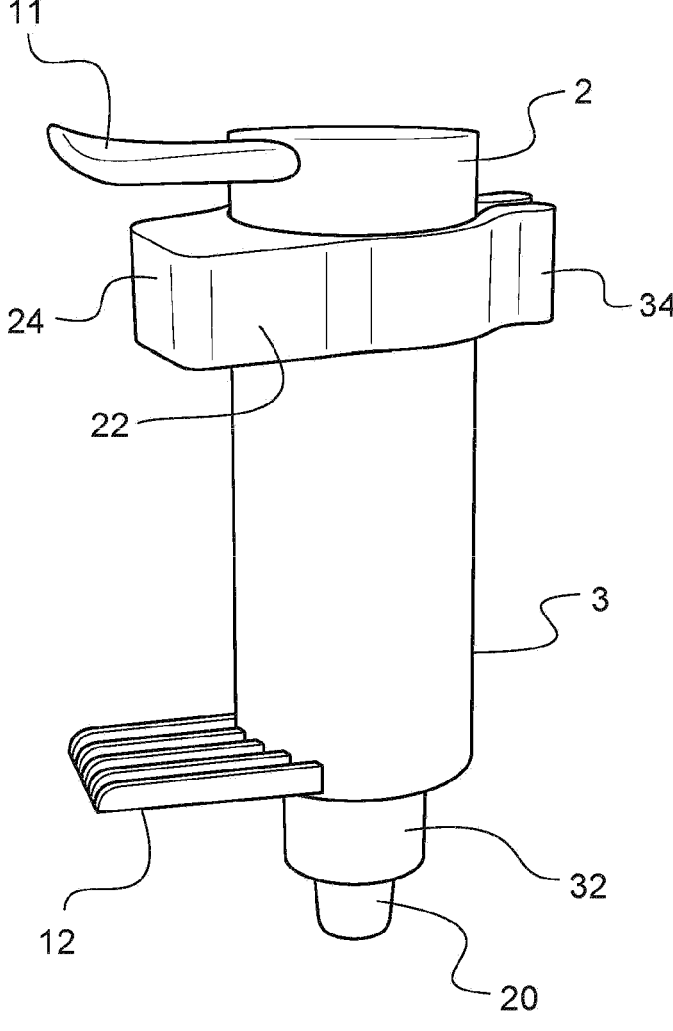
FIG. 9 represents, according to a schematic three-dimensional view, an electronic module according to another embodiment of the invention installed on a vial similar to that of FIGS. 3 and 4.

More specifically, in the embodiment represented in FIG. 9, the electronic module 22 is clipped on the dispensing head on the second portion of the delivery assist device 14 which cooperates with the movable portion 6. To this end, the electronic module 22 is provided with two large fastening legs 34 which clasp the extreme portion of the second portion of the delivery system 14. The case 24 of the electronic module 22 covers, in the example represented herein the groove 15 and the pin 16 of the first portion of the delivery system 13 which is guided in the groove 15. The pin 16 may be used to actuate the actuator of the electronic module (not visible in FIG. 9, because located on the face of the case 24 which is in contact with the vial 1). The movement of the pin 16 in the groove 15, which reflects the movement of the movable portion 6 relative to the main body 2, results in the movement of the actuator of the module 22 and reflects an installation of product by the vial.

The transmission, in real-time or not, of the data originating from the electronic module allows controlling the parameters of installation of the product and compliance with the treatment. The transmission is carried out to a computer equipment, for example a computer, a server, a tablet or a smartphone (generally referred to as "smartphone"). The computer equipment executes software enabling the recovery, processing, and display of data (raw or after processing) derived from the electronic module 22 (or several modules).

FIGS. 10 to 13 represent various tabs of an application executed on a smartphone connected to the electronic module 22. These different tabs illustrate, as examples, different functionalities that could be offered by the electronic module 22 and the executed application.

Figure 10:
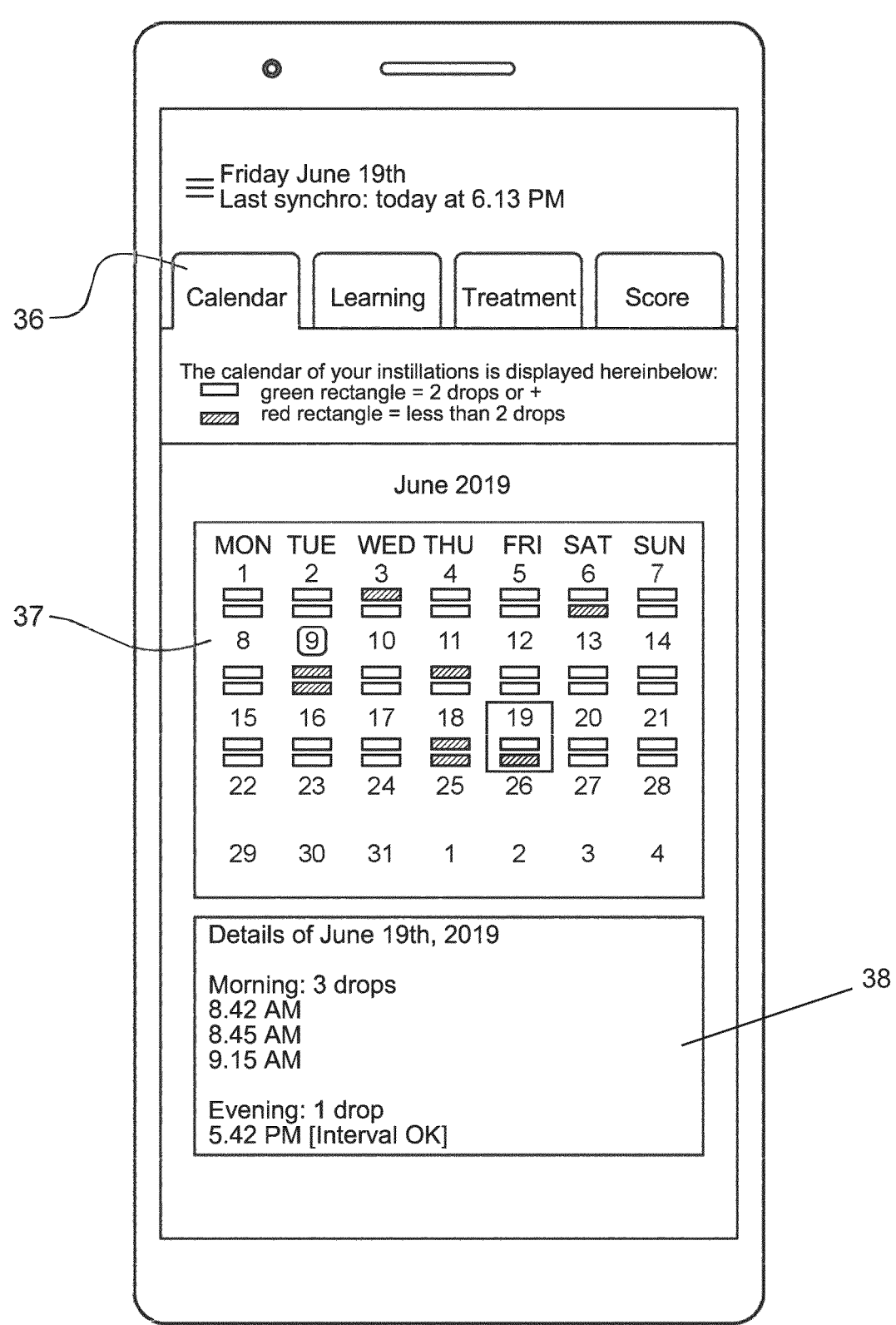
FIG. 10 represents, according to a schematic representation, an example of a first tab of an application interface that could be implemented in the invention.

FIG. 10 represents a "calendar" tab 36 dedicated to the control of compliance with a treatment over time. Depending on the dosage indicated elsewhere in the application (cf. FIG. 12 described hereinafter), this calendar tab 36 offers a general temporal view of compliance with the treatment. In particular, the calendar tab could offer a monthly (or alternatively, weekly, over two weeks, etc.) view 37. For each day is represented a rectangle corresponding to a scheduled installation (for example, for one installation in the morning and one installation in the evening, two rectangles are represented for each day). For correctly completed installations, a visual indicator, herein in the form of a white rectangle, is displayed. Of course, other indicators, and/or other colours may be used. In particular, a green indicator is spontaneously associated with a positive action, and could therefore advantageously represent a correct installation. By correct installation, it should be understood the detection of an actuation of the vial within a given time frame, or where appropriate several actuations of the vial corresponding to the number of drops to be delivered, and/or the detection within the given time frame of an adequate orientation of the vial.

Conversely, an incorrect installation is represented by a different indicator, herein a hatched rectangle. Of course, other indicators, and or other colours may be used. In particular, a red indicator is spontaneously associated with a negative action, and could therefore advantageously represent an incorrect installation.

An action (click, pointing, press) on a day in the monthly view 37 allows the display of details on the installations of this day, in a detail area 38. For example, the detail area could provide the exact time of delivery of each drop, other information such as the correct compliance, or not, with the interval provided for in the treatment dosage, or else various information related to possible errors in the system, the measurement, etc.

Figure 11:
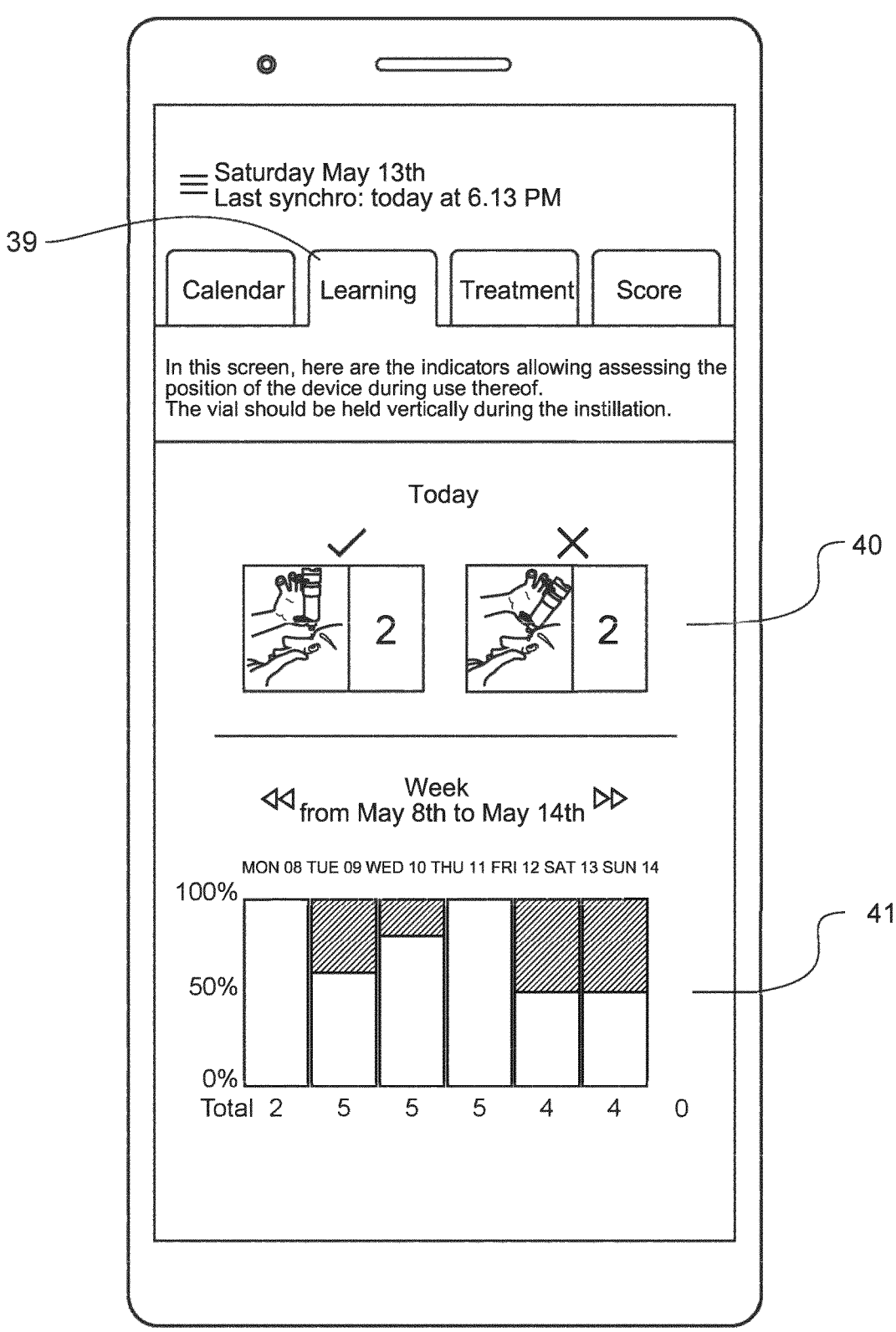
FIG. 11 represents, according to a schematic representation, an example of a second tab of an application interface that could be implemented in the invention.

FIG. 11 shows an "education" tab 39, dedicated to the control and learning by the user of the correct installation gestures. This tab allows indicating, in some embodiments, whether an installation has been carried out with the vial correctly oriented, i.e. with its main axis A correctly aligned with the vertical. The result could be displayed in real-time, immediately after the actuation of the vial, which enables the user to correct the vial position for the next actuation of the vial.

Different views regarding past instillations may be available in this tab. In the example represented herein, a daily view 40 indicates the number of instillations carried out with a correct orientation and the number of instillations carried out with an incorrect orientation during the current day. In the represented example, a weekly view 41 provides information on the proportion of instillations carried out with a correct orientation and the proportion of instillations carried out with an orientation over the current week, or over a rolling week, or more generally over several days. For example, the dispense represented for each day by a histogram, the instillations carried out with a correct orientation being represented by a white bar, and the instillations carried out with an incorrect orientation being represented by a hatched bar. Other indicators and/or other colours (for example green and red) may be used.

Other categories may be illustrated, for example instillations carried out with a limit orientation or an uncertain orientation (for example represented by an orange indicator).

One of the objectives of this education tab 39 is to enable the user to verify whether the orientation imparted on the vial during the instillation of ophthalmic drops is acceptable, and to correct this orientation if necessary throughout his treatment.

Figure 12:
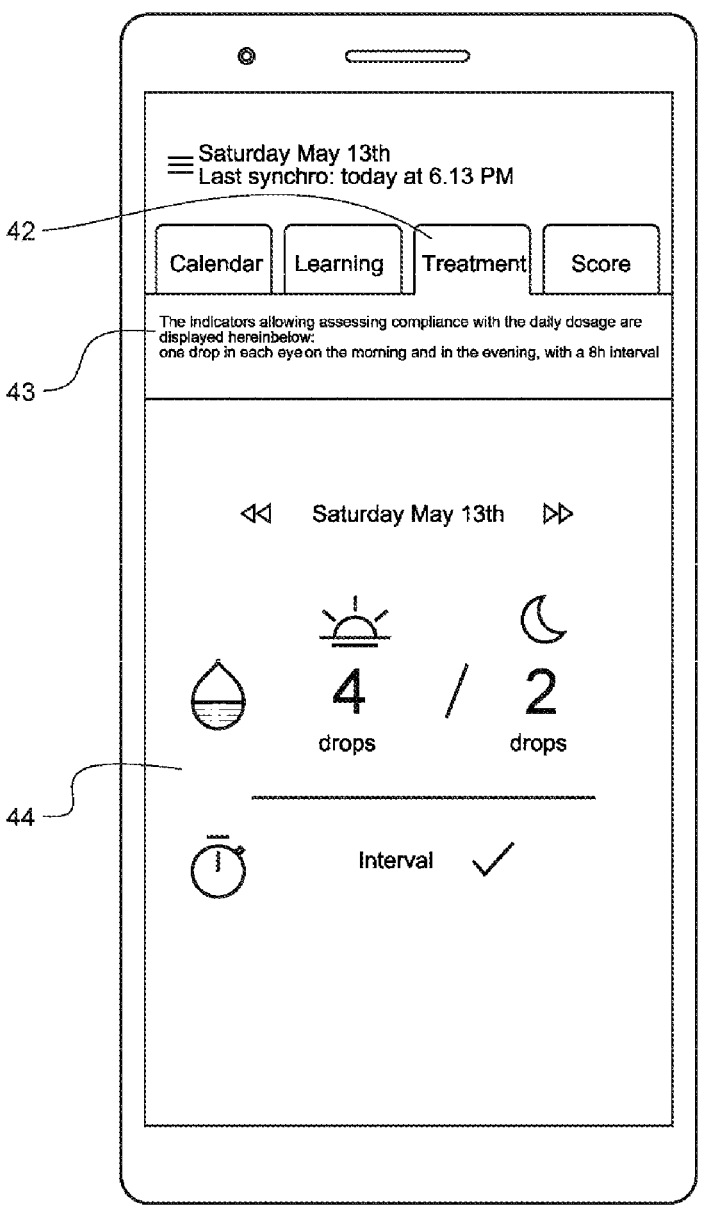
FIG. 12 represents, according to a schematic representation, an example of a third tab of an application interface that could be implemented in the invention.

FIG. 12 represents a "treatment" tab 42, dedicated to the visualisation and, where appropriate, to the determination of the dosage. In particular, this tab could be used to program the dosage of the treatment, which will be used by the other tabs.

This tab also presents a reminder of the dosage 43. It also presents a dosage control area, which indicates the number of drops dispensed in comparison with the desired dosage, and which indicates whether the interval between two instillations is complied with (i.e. located within an admissible time range). The control of the interval is important, for example, when the user travels to different time zones, so that monitoring of the treatment based on local time alone is not enough.

Figure 13:
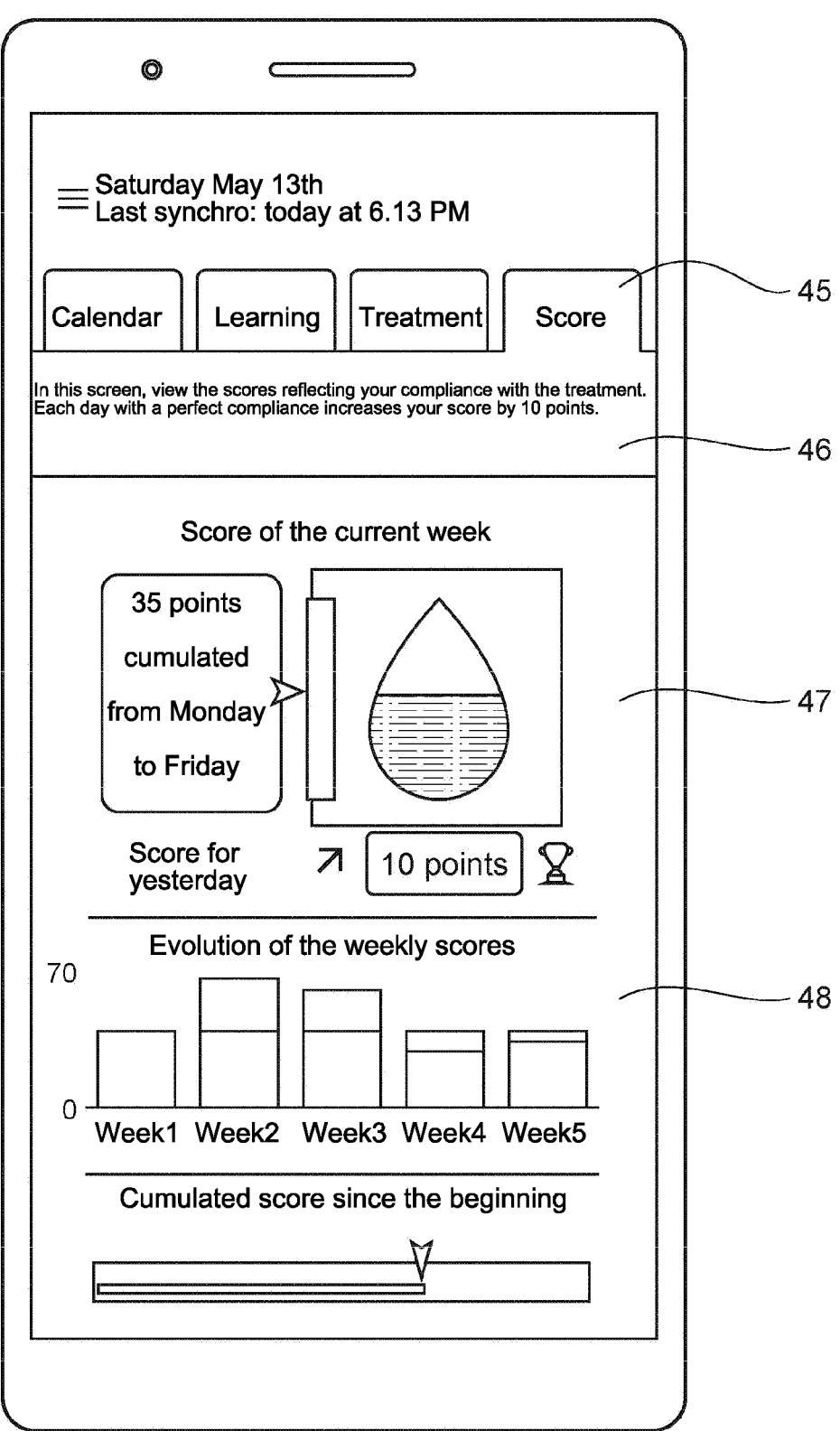
FIG. 13 represents, according to a schematic representation, an example of a fourth tab of an application interface that could be implemented in the invention.

FIG. 13 represents a "score" tab 45. The score tab 45 processes and consolidates the data received from the electronic module 22 to calculate a score, in the form of points, of colour, of progress on a scale, etc., which reflects proper compliance with the treatment. This proper compliance consists in complying with the prescribed dosage, but also in adopting a correct instillation gesture (reflected by the proper orientation of the vial when dispensing the ophthalmic product). It is primarily a funny way to incite the user to follow his treatment as best as possible, by inciting him, consciously or not, to improve his score. The score tab may include a reminder of the used calculation rule 46. The score tab has a display area of the weekly score 47 (current week or rolling week).

The score of each week may be memorised, so as to present the evolution of the weekly scores in an evolution area of the scores 48. Finally, a cumulative score area 49 presents a score based on the entire treatment, for example in the form of a progress bar or a slider indicating an average compliance score.

The module thus described enables the detection of the actuations of a vial with a mechanical pump, in particular with axial actuation (according to a main axis of the vial). The detection of the actuations, coupled with temporal information (actuation time point, intervals between the actuations) as well as, where necessary, with information regarding the orientation of the vial during the actuation of its pump, allows controlling the compliance and quality of instillation of a treatment, according to the prescribed dosage. The fact that the module is independent of the vial offers multiple advantages. For example, the module may be transferred on several vials during a long-term treatment. The module may be prescribed to only some patients: patients likely to forget to follow their treatment, patients likely to doubt after a few moments whether or not they have instilled the ophthalmic product, patients starting a treatment. Furthermore, it is possible to equip a pre-existing vial, i.e. already on the market, only when this is desired or necessary. Thus, without rebuilding a range of ophthalmic products, it is possible to offer the same vial without a module or with an independent module, depending on the product contained in the vial, depending on the market (geographic area), etc.

The module could also enable the user to learn the correct instillation gestures, necessary for a good effectiveness of the treatment. When the electronic module is linked, for example paired, with computer equipment executing appropriate software, for example a smartphone executing a dedicated application, the data obtained by the electronic module and transferred to the electronic equipment could be processed to characterise compliance with the treatment, and, where appropriate, ask the user to improve it.

The invention claimed is:

1. A method for monitoring compliance with an ophthalmic therapeutic treatment, the method comprising:

providing an ophthalmic product vial and a device configured to monitor compliance with an ophthalmic therapeutic treatment, the device comprising an external computer equipment, and an electronic module configured to detect data relating to an actuation of a mechanical pump of a vial of a liquid ophthalmic product including a main body including a reservoir, a dispensing head, and a mechanical pump, the dispensing head being mounted on the main body, the dispensing head including a movable portion a movement of which relative to the main body actuates the mechanical pump to sample the liquid ophthalmic product present in the reservoir, the electronic module being independent of said vial so that the electronic module is configured to be attached and fastened therein, the electronic module including an actuator configured to be set in motion by the movement of the movable portion, a sensor configured to be actuated by the movement of the actuator, an orientation sensor configured to provide information relating to its orientation, and a wired or wireless communication port configured to transfer data relating to the actuation of the mechanical pump of the vial and the data relating to its orientation towards an external computer equipment, fastening the electronic module on the ophthalmic product vial;

determining, over time, correct product instillations and incorrect product instillations, according to compliance parameters including a detection, within a specific time frame, of one or more actuations of the vial and a detection of a correct orientation of the vial;

providing a user with the results of the determining the correct product instillations and the incorrect product instillations;

calculating a compliance score as a function of the compliance parameters, the compliance score being a mark in a form of one of points, a color, and a level on a scale, the compliance score reflecting a proper compliance with the ophthalmic therapeutic treatment, the proper compliance including complying with the prescribed dosage and adopting a proper orientation of the vial when dispensing the ophthalmic product; and indicating the calculated compliance score to the user, wherein said external computer equipment is configured to communicate with said electronic module, the external computer equipment executing software enabling temporal monitoring of the actuations of the actuator of the electronic module, which correspond to a delivery of the ophthalmic product, the external computer equipment being configured to provide the user with information on the correct or incorrect orientation of the electronic module, and therefore accordingly of the vial equipped with said electronic module, when the actuator is actuated, the external computer equipment executing the software being configured to calculate, based on the data transmitted by the electronic module, the compliance score and indicate the compliance score to the user.

2. The method for monitoring compliance with the ophthalmic therapeutic treatment according to claim 1, further comprising:

informing the user on a temporal progression of said compliance score.

3. The method for monitoring compliance with the ophthalmic therapeutic treatment according to claim 1, wherein the information on the correct or incorrect orientation of the electronic module includes visual information.

4. The method for monitoring compliance with the ophthalmic therapeutic treatment according to claim 1, wherein the information on the correct or incorrect orientation of the electronic module includes audible information.

5. The method for monitoring compliance with the ophthalmic therapeutic treatment according to claim 1, further comprising emitting in real-time a signal indicating that the electronic module has the correct orientation to dispense a liquid ophthalmic product by the vial equipped with said electronic module.

6. The method for monitoring compliance with the ophthalmic therapeutic treatment according to claim 1, further comprising transferring the data towards the external computer equipment according to a Bluetooth™ protocol.

7. The method for monitoring compliance with the ophthalmic therapeutic treatment according to claim 1, further comprising storing, by an electronic memory of the electronic module, data relating to the actuations of the actuator.

8. The method for monitoring compliance with the ophthalmic therapeutic treatment according to claim 1, further comprising recording a dosage and providing the user with a comparison between the recorded dosage and the data relating to the actuation of the actuator of the electronic module transmitted to the external computer equipment.

* * * * *